US012730053B2

(12) United States Patent
Chu et al.

(10) Patent No.: US 12,730,053 B2
(45) Date of Patent: Sep. 8, 2026

(54) SMOKE DETECTOR WITH ANTI-INSECT FUNCTION AND SPOILER FUNCTION

(71) Applicant: PixArt Imaging Inc., Hsin-Chu City (TW)

(72) Inventors: Yen-Chang Chu, Hsin-Chu City (TW); Cheng-Nan Tsai, Hsin-Chu City (TW); Chih-Ming Sun, Hsin-Chu City (TW); Zhi-Hao Wu, Hsin-Chu City (TW); Hung-Yu Lai, Hsin-Chu City (TW)

(73) Assignee: PixArt Imaging Inc., Hsin-Chu City (TW)

( * ) Notice: Subject to any disclaimer, the term of this patent is extended or adjusted under 35 U.S.C. 154(b) by 141 days.

(21) Appl. No.: 18/422,024

(22) Filed: Jan. 25, 2024

(65) Prior Publication Data

US 2024/0159642 A1 May 16, 2024

Related U.S. Application Data

(63) Continuation-in-part of application No. 17/883,625, filed on Aug. 9, 2022, now Pat. No. 12,148,279.

(30) Foreign Application Priority Data

Mar. 20, 2023 (TW) ................................ 112202450

(51) Int. Cl.
*G01N 15/075* (2024.01)
*G01N 33/00* (2006.01)

(52) U.S. Cl.
CPC ....... *G01N 15/075* (2024.01); *G01N 33/0027* (2013.01)

(58) Field of Classification Search
CPC .................................................. G08B 17/107
(Continued)

(56) References Cited

U.S. PATENT DOCUMENTS 6,195,014 B1 * 2/2001 Sakurai ................ G08B 17/113 340/630
6,522,254 B1 * 2/2003 Yamano ............... G08B 17/107 340/630

(Continued)

FOREIGN PATENT DOCUMENTS

CN 108106978 6/2018
CN 208156817 11/2018

(Continued)

*Primary Examiner* — Travis R Hunnings
(74) *Attorney, Agent, or Firm* — Winston Hsu

(57) ABSTRACT

A smoke detector with an anti-insect function includes a substrate, an optical detection module, a top cover, a base and a perforated plate. The substrate has a ring shape region surrounding a central detection region, and a first block structure of the central detection region is protruded from the substrate and higher than an upper surface of the ring shape region. The optical detection module is disposed inside the central detection region. The top cover has a lateral wall. The base is disposed on the substrate and connected to the top cover to cover the optical detection module. The base has a second block structure partly overlapped with the lateral wall to form a guiding channel. The perforated plate is disposed between the lateral wall and the second block structure to prevent an insect from moving into the top cover through the guiding channel.

9 Claims, 9 Drawing Sheets

(58) Field of Classification Search
USPC .......................................................... 340/630
See application file for complete search history.

(56) References Cited

U.S. PATENT DOCUMENTS

| | | | | |
|---|---|---|---|---|
| 6,967,582 | B2 | 11/2005 | Tice | |
| 7,205,901 | B2 | 4/2007 | Demster | |
| 2002/0084907 | A1* | 7/2002 | Rattman | G08B 17/113 340/630 |
| 2002/0154018 | A1* | 10/2002 | Nishikawa | G08B 17/06 340/630 |
| 2005/0134468 | A1* | 6/2005 | Thomas | G08B 29/18 340/630 |
| 2006/0007010 | A1* | 1/2006 | Mi | G08B 29/20 340/630 |
| 2021/0041350 | A1* | 2/2021 | Takano | G08B 17/113 |

FOREIGN PATENT DOCUMENTS

| | | |
|---|---|---|
| CN | 209103484 | 7/2019 |
| CN | 111080960 | 4/2020 |
| CN | 210863533 | 6/2020 |
| CN | 215868100 | 2/2022 |
| JP | 2011-215705 A | 10/2011 |
| JP | 2018-106804 A | 7/2018 |
| TW | 1621846 | 4/2018 |

* cited by examiner

FIG. 7

SMOKE DETECTOR WITH ANTI-INSECT FUNCTION AND SPOILER FUNCTION

CROSS REFERENCE TO RELATED APPLICATIONS

This application is a continuation-in-part of U.S. application Ser. No. 17/883,625, filed on Aug. 9, 2022. The content of the application is incorporated herein by reference.

BACKGROUND OF THE INVENTION

1. Field of the Invention

The present invention relates to a smoke detector, and more particularly, to a smoke detector with an anti-insect function and a spoiler function.

2. Description of the Prior Art

A conventional optical smoke detection device includes a circuit board, an optical detector and a housing. The optical detector is disposed on the circuit board. The housing is installed on the circuit board to cover the optical detector. The conventional optical smoke detection device forms a plurality of holes on the housing. External gaseous matter flows into and out of the housing through the holes. The optical detector projects an optical signal onto the gaseous matter inside the housing, and detects variation of scattering parameters resulted from the illuminated gaseous matter to determine concentration of the gaseous matter. However, an insect may crawl into the housing through the holes due to ambient light projected into the housing through the holes, so that a detection accuracy of the optical detector is decreased accordingly. Therefore, design of a smoke detector with preferred smoke conductivity and preferred gaseous permeability and without interference from the ambient light and the common insects is an important issue in the mechanical design industry.

SUMMARY OF THE INVENTION

The present invention provides a smoke detector with an anti-insect function and a spoiler function for solving above drawbacks.

According to the claimed invention, a smoke detector with an anti-insect function includes a substrate, an optical detection module, a top cover, a base and a perforated plate. The substrate has a ring shape region surrounding a central detection region, and a first block structure of the central detection region is protruded from the substrate and higher than an upper surface of the ring shape region. The optical detection module is disposed inside the central detection region. The top cover has a lateral wall. The base is disposed on the substrate and connected with the top cover and adapted to cover the optical detection module. The base has a second block structure partly overlapped with the lateral wall to form a guiding channel. The perforated plate is disposed between the lateral wall and the second block structure, and adapted to prevent an insect from moving into the top cover through the guiding channel.

According to the claimed invention, the perforated plate is a ring-typed structure, an inner edge of the ring-typed structure corresponds to the lateral wall, an outer edge of the ring-typed structure corresponds to the second block structure, a plurality of holes is formed on a plate body of the ring-typed structure set between the inner edge and the outer edge.

According to the claimed invention, the central detection region comprises a sunken structure, the optical detection module is disposed inside the sunken structure, and a hollow area formed by the inner edge of the ring-typed structure corresponds to the optical detection module. The inner edge and the outer edge of the ring-typed structure respectively abuts against the lateral wall and the second block structure. A thickness of the plate body is greater than or equal to an aperture of each of the plurality of hole.

According to the claimed invention, the top cover further comprises a cover body connected to the lateral wall, the lateral wall and the cover body both have an airtight feature, and the perforated plate is attached to a side of the lateral wall opposite to the cover body. The smoke detector further includes a plurality of connection ribs. Two opposite ends of each of the plurality of connection ribs are connected to an inner surface of the base and an outer surface of the top cover respectively, and the perforated plate is attached to the plurality of connection ribs.

According to the claimed invention, the perforated plate is connected to the top cover and the base in a monolithically integrated manner, or the perforated plate is disposed between the top cover and the base in a detachable manner.

According to the claimed invention, a smoke detector with a spoiler function includes a substrate, an optical detection module, a top cover, a base and a spoiler element. The substrate has a ring shape region surrounding a central detection region. The optical detection module is disposed inside the central detection region. The top cover has a lateral wall. The base has a connection rib connected to the top cover, and is disposed on the ring shape region of the substrate to cover the optical detection module by the lateral wall of the top cover. The spoiler element is disposed on a side of the base opposite to the substrate for covering a guiding channel formed between the top cover and the base via the connection rib, and the spoiler element has a guiding hole structure with asymmetric design connected to the guiding channel.

According to the claimed invention, the guiding hole structure is disposed on a side of the spoiler element opposite to the base, and an inlet and an outlet of the guiding hole structure are connected to an inner space of the base through the guiding channel.

According to the claimed invention, an inner side and an outer side of the spoiler element respectively abut against the lateral wall of the top cover and the second block structure of the base. The spoiler element is attached to the connection rib. The spoiler element is integrated with the top cover and the base monolithically, or the spoiler element is detachably assembled with the top cover and the base.

According to the claimed invention, the spoiler element further has a plurality of guiding hole structures, a number of the guiding hole structures is an odd number, any two of the plurality of guiding hole structures have different hole sizes, and an interval between any two adjacent guiding hole structures is different from an interval between other adjacent guiding hole structures.

The present invention can utilize the substrate, the base and the top cover to form the case of the smoke detector. The optical detection module can be disposed on the central detection region of the substrate and surrounded by the first block structure. The second block structure of the base can be partly overlapped with the lateral wall of the top cover. The perforated plate can be disposed between the lateral wall and the second block structure, and used to shield the guiding channel formed between the base and the top cover. The aperture of the hole on the perforated plate can be smaller than the size of the common insects, and can avoid the insect from passing through the guiding channel to enter the top cover. The perforated plate can be detachable, or integrated with other structural components. Therefore, the present invention can replace the original perforated plate by another perforated plate having the holes with the suitable aperture and the suitable distribution density in accordance with the insect species lived in the place where on the smoke detector is installed, for preferred anti-insect function.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 7 is an exploded diagram of a smoke detector according to another embodiment of the present invention.

DETAILED DESCRIPTION

Figure 1:
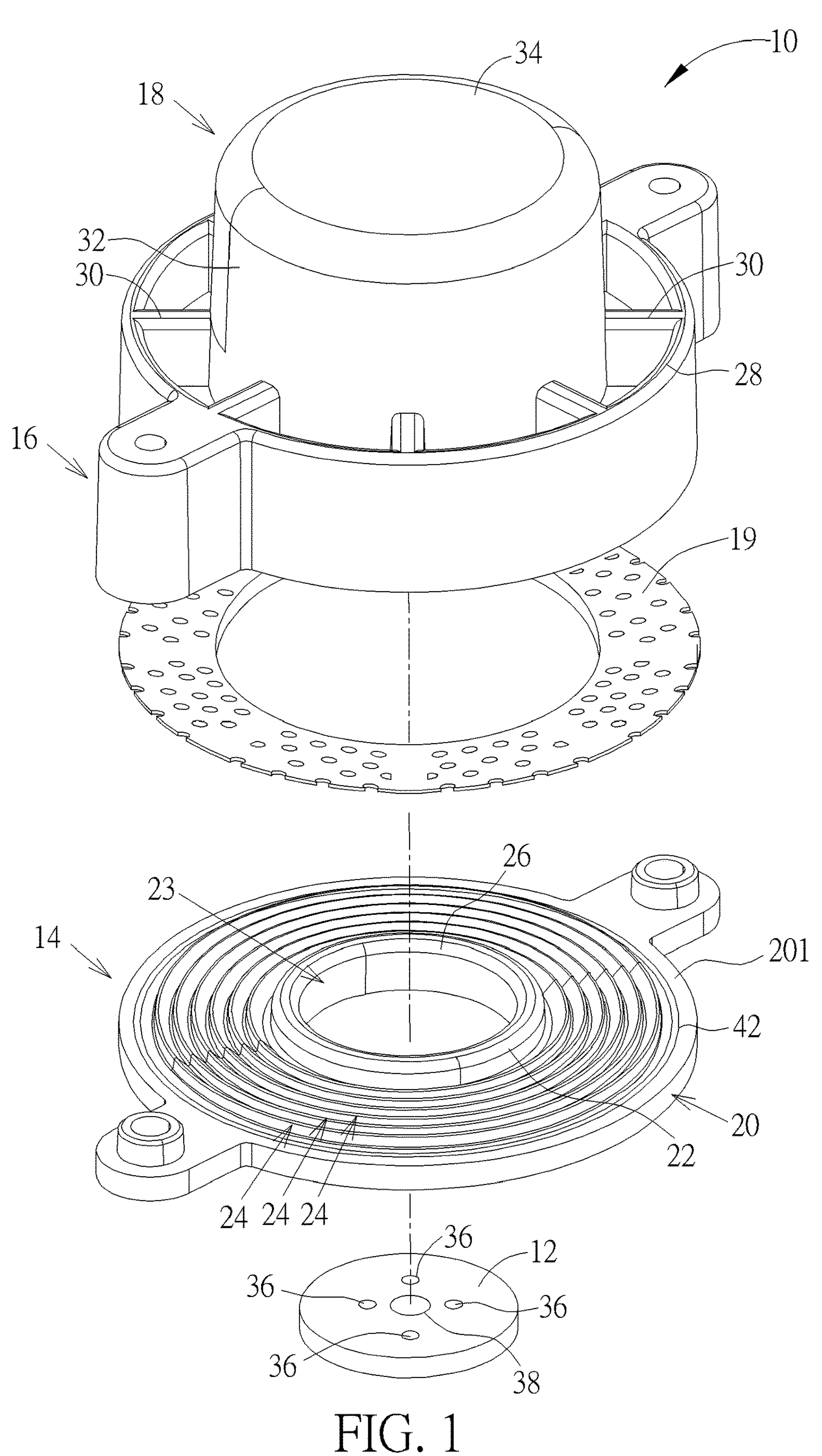
FIG. 1 is an exploded diagram of parts of a smoke detector according to an embodiment of the present invention.

Please refer to FIG. 1. FIG. 1 is an exploded diagram of parts of a smoke detector 10 according to an embodiment of the present invention. The smoke detector 10 can include an optical detection module 12, a substrate 14, a base 16, a top cover 18 and a perforated plate 19. The optical detection module 12 can be disposed inside a cavity formed on the substrate 14 and therefore the optical detection module 12 and the substrate 14 are coplanar, or optical detection module 12 can be disposed on the substrate 14 and located between the substrate 14 and the base 16. The top cover 18 and the base 16 can be assembled with each other and then disposed on the optical detection module 12. A guiding channel can be formed between the base 16 and the top cover 18. External gaseous can flow into and out of the smoke detector 10 through the guiding channel. The optical detection module 12 can analyze variation of scattering parameters of an optical signal to determine concentration of gaseous matter passing through the smoke detector 10. The case of the present invention can have advantages of high smoke conductivity and high gaseous permeability for effectively restraining interference of ambient light, so as to prevent a detection accuracy of the optical detection module 12 from being affected by variation of the ambient light.

The case can include a substrate 14, a base 16 and a top cover 18. The substrate 14 can have a ring shape region 20 and a central detection region 22. The optical detection module 12 can be disposed in the central detection region 22. The central detection region 22 can be a hollow element (which can be shown in FIG. 1) or a solid element (which is not shown in the figures). When the central detection region 22 is the hollow element and the smoke detector 10 is assembled with a circuit board (which is not shown in the figures), the optical detection module 12 can pierce through the central detection region 22 and be directly disposed on the circuit board. When the central detection region 22 is the solid element, the optical detection module 12 can be directly disposed on the central detection region 22, and a transmission cable (which is not shown in the figures) passes through the substrate 14 to electrically connect with the circuit board. A type of the central detection region 22 is not limited to the embodiment shown in FIG. 1, and depends on a design demand. The central detection region 22 can have a sunken structure 23, and the sunken structure 23 can be the cavity of the hollow element or a central sunken area of the solid element. The optical detection module 12 can be disposed inside the sunken structure 23.

The ring shape region 20 can be disposed around the central detection region 22. The ring shape region 20 can have a plurality of grooves 24, and each of the plurality of grooves 24 can surround the central detection region 22 as a concentric circle. A width, a depth and a shape of the groove 24 are not limited to the embodiment shown in FIG. 1, which depend on the design demand. The central detection region 22 can include a first block structure 26 protruded from the substrate 14. A top of the first block structure 26 can be higher than an upper surface of the optical detection module 12 to avoid the interference of the ambient light. Besides, the top of the first block structure 26 can be higher than an upper surface 201 of the ring shape region 20 and a top end of the groove 24. The top end of the groove 24 can be higher than the upper surface 201 of the ring shape region 20, and a bottom end of the groove 24 can be lower than the upper surface 201 of the ring shape region 20. Actual relation between the first block structure 26, the ring shape region 20 and the groove 24 is not limited to the foresaid embodiment, and depends on the design demand.

The base 16 can be disposed on the substrate 14 to surround the optical detection module 12, so as to provide a protection function and artistic decoration. The base 16 can have a second block structure 28 disposed on the outer edge of the substrate 14 as a ring. The second block structure 28 can be spaced from the top cover 18. The smoke detector 10 can further include a plurality of connection ribs 30. Two opposite ends of each connection rib 30 can be respectively connected to the inner surface of the base 16 (which means an inner lateral surface of the second block structure 28) and an outer surface of the top cover 18, and a plurality of openings can be formed between the substrate 14 and the base 16. The top cover 18 can be connected to the second block structure 28 via the connection ribs 30. The smoke detector 10 can utilize the lateral wall 32 of the top cover 18, the second block structure 28 of the base 16, and the connection rib 30 to form the guiding channel composed of the plurality of openings. It should be mentioned that the lateral wall 32 can be partly overlapped with the second block structure 28, which means a bottom of the lateral wall 32 can be lower than a top of the second block structure 28, or the top cover 18 can be partly inserted into the second block structure 28 of the base 16, so that smoke goes through the guiding channel to enter the smoke detector 10. The top cover 18 partly inserting into the second block structure 28 can be interpreted as: some part of the lateral wall 32 is not parallel to the second block structure 28, and the foresaid part of the lateral wall 32 can obliquely abut against the second block structure 28; besides, the guiding channel can be kept smooth as if the connection ribs 30 is connected between the base 16 and the top cover 18 and/or a hole is formed on connection where the lateral wall 32 obliquely abuts against the second block structure 28.

The top cover 18 can include a lateral wall 32 and a cover body 34 connected with each other, and can be used to cover the optical detection module 12. The top cover 18 does not have holes and is made by airtight material, so to as have an airtight feature. An inner part of the top cover 18 can be a chamber formed by the lateral wall 32 and the cover body 34. The gaseous matter entering the smoke detector 10 through the guiding channel can be gathered inside the chamber of the top cover 18, and then be exhausted out of the smoke detector 10 through the guiding channel. The optical detection module 12 can detect the variation of scattering parameters of the optical signal resulted from the gaseous matter gathered inside the top cover 18. The base 16, the top cover 18 and the connection rib 30 can be independent elements, and can be assembled with each other in a detachable manner; besides, the base 16 can be monolithically integrated with the top cover 18 and the connection rib 30. Structural relation between the base 16, the top cover 18 and the connection rib 30 is not limited to the foresaid embodiments, and depends on the design demand. The optical detection module 12 can include an optical emitter 36 and an optical receiver 38. Numbers and positions of the optical emitter 36 and the optical receiver 38 are not limited to the embodiment shown in FIG. 1, and depend on the design demand. The optical emitter 36 can emit an illumination beam into the top cover 18. The illumination beam can be projected onto the gaseous matter gathered inside the top cover 18 to result in a scattering phenomenon. The optical receiver 38 can receive and analyze the variation of the scattering parameters resulted from the illumination beam projected onto the gaseous matter, so as to determine the concentration of the gaseous matter passing through the smoke detector 10.

As shown in FIG. 1, the guiding channel of the smoke detector 10 can have a large aperture for allowing rapid pass of the gaseous matter, and the aperture of the guiding channel may be greater than a size of the common insects. Therefore, the smoke detector 10 can dispose the perforated plate 19 between the lateral wall 32 and the second block structure 28, or dispose the perforated plate 19 on any position that can cover the guiding channel, and utilize the perforated plate 19 to avoid the insect from entering the top cover 18 through the guiding channel.

Figure 2:
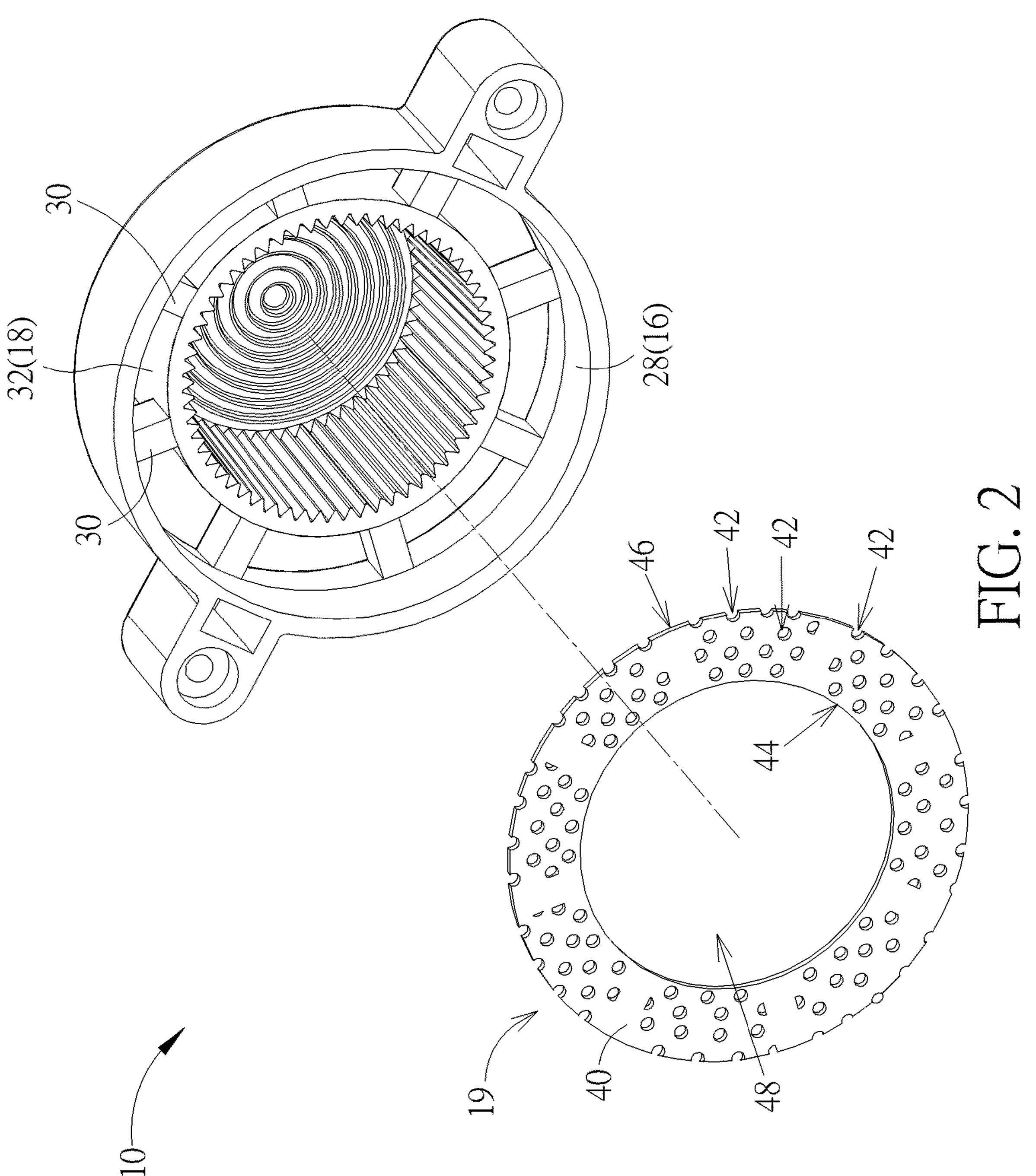
FIG. 2 and FIG. 3 are diagrams of a partial case of the smoke detector and a perforated plate in different view angles according to a first embodiment of the present invention.
Figure 3:
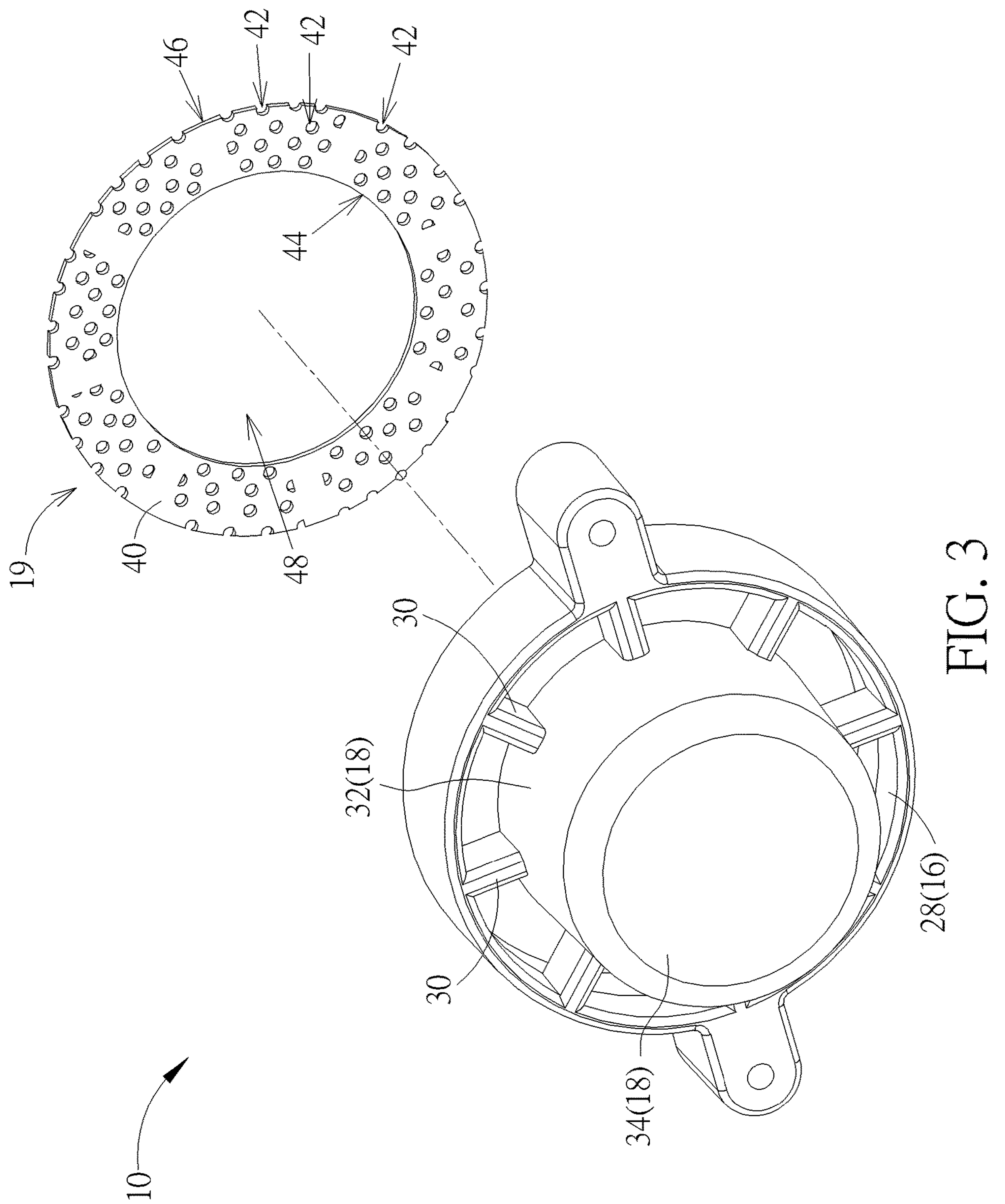

Please refer to FIG. 2 and FIG. 3. FIG. 2 and FIG. 3 are diagrams of the partial case of the smoke detector 10 and the perforated plate 19 in different view angles according to a first embodiment of the present invention. The perforated plate 19 can be a ring-typed structure; a plurality of holes 42 can be formed on a plate body 40 of the ring-typed structure, and an aperture of the hole 42 can be smaller than the size of the common insects, such as 2 mm or 3 mm, for preventing pass of the insect. An aperture size and distribution of the hole 42 are not limited to the embodiment shown in FIG. 2 and FIG. 3, and depend on the design demand. In addition, the ring-typed structure of the perforated plate 19 can have an inner edge 44 and an outer edge 46. A hollow area 48 formed by the inner edge 44 can correspond to the optical detection module 12. The inner edge 44 and the outer edge 46 can respectively correspond to the lateral wall 32 and the second block structure 28.

In the first embodiment, the perforated plate 19 can be disposed between the top cover 18 and the base 16 in a detachable manner; for example, the inner edge 44 of the perforated plate 19 can abut against a side of the lateral wall 32 opposite to the cover body 34, and the outer edge 46 of the perforated plate 19 can abut against an inner lateral surface of the second block structure 28. Moreover, the plate body 40 of the perforated plate 19 may abut against the connection rib 30 between the base 16 and the top cover 18. There is no gap formed between the perforated plate 19, the second block structure 28, the connection rib 30 and the lateral wall 32, and the smoke detector 10 can provide the enhanced anti-insect function.

Figure 4:
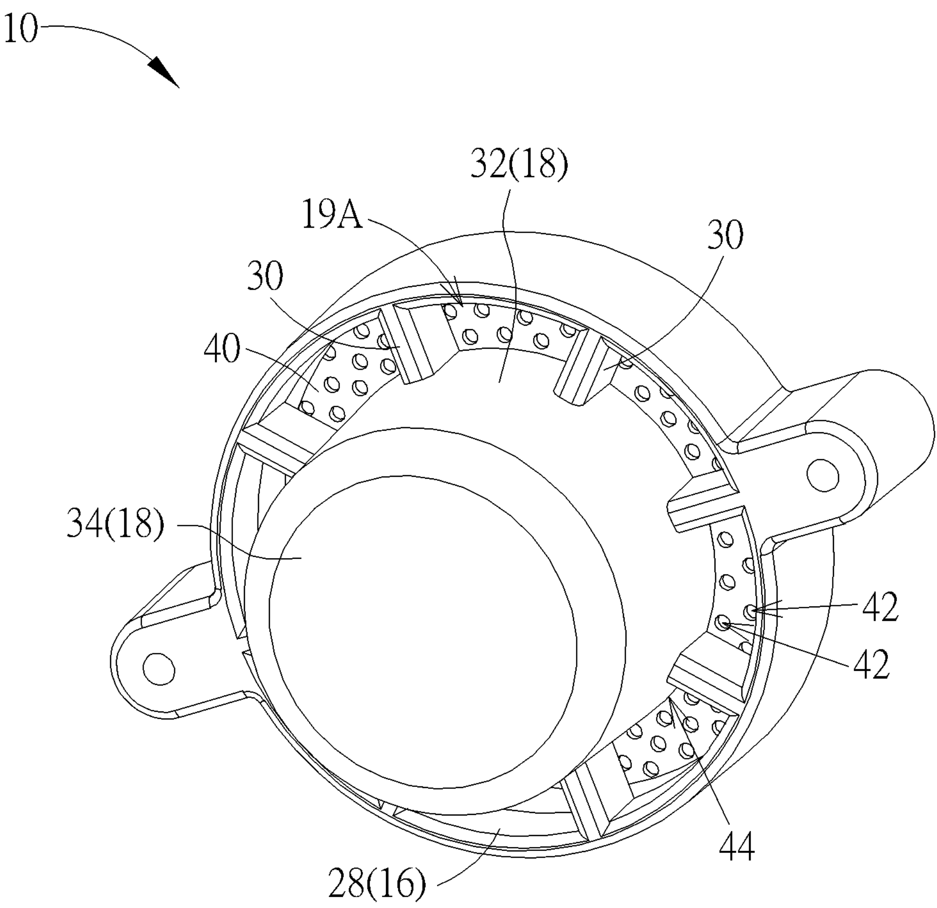
FIG. 4 and FIG. 5 are diagrams of the partial case of the smoke detector and the perforated plate according to a second embodiment of the present invention.
Figure 5:
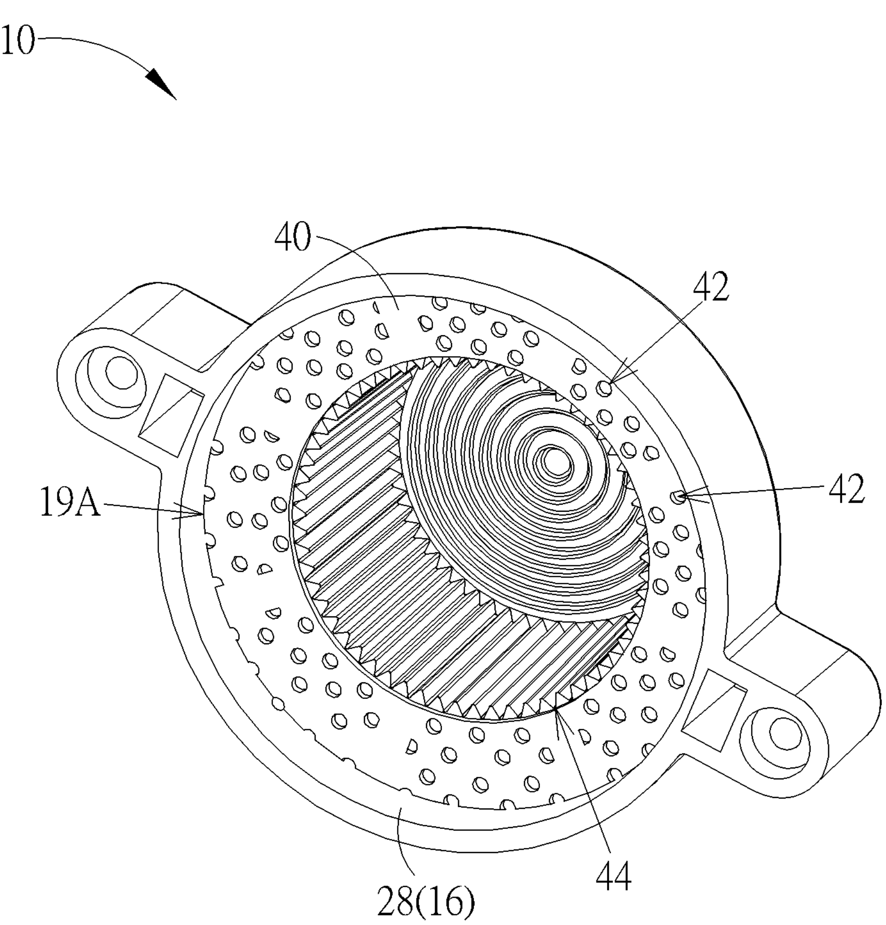

Please refer to FIG. 4 and FIG. 5. FIG. 4 and FIG. 5 are diagrams of the partial case of the smoke detector 10 and the perforated plate 19A according to a second embodiment of the present invention. In the second embodiment, elements having the same numerals as ones of the first embodiment can have the same structures and functions, and a detailed description is omitted herein for simplicity. The perforated plate 19A can be the ring-typed structure, and have the plate body 40, the hole 42, the inner edge 44 and the outer edge 46. The perforated plate 19A can be manufactured with the case; for example, the perforated plate 19A can be connected with the top cover 18 and the base 16 in a monolithically integrated manner. The inner edge 44 and the outer edge 46 of the perforated plate 19A can be respectively attached to the lateral wall 32 and the second block structure 28, and the plate body 40 of the perforated plate 19A can be attached to the connection rib 30, so that there is no gap formed between the perforated plate 19A, the second block structure 28, the connection rib 30 and the lateral wall 32 for pass of the insect.

Figure 6:
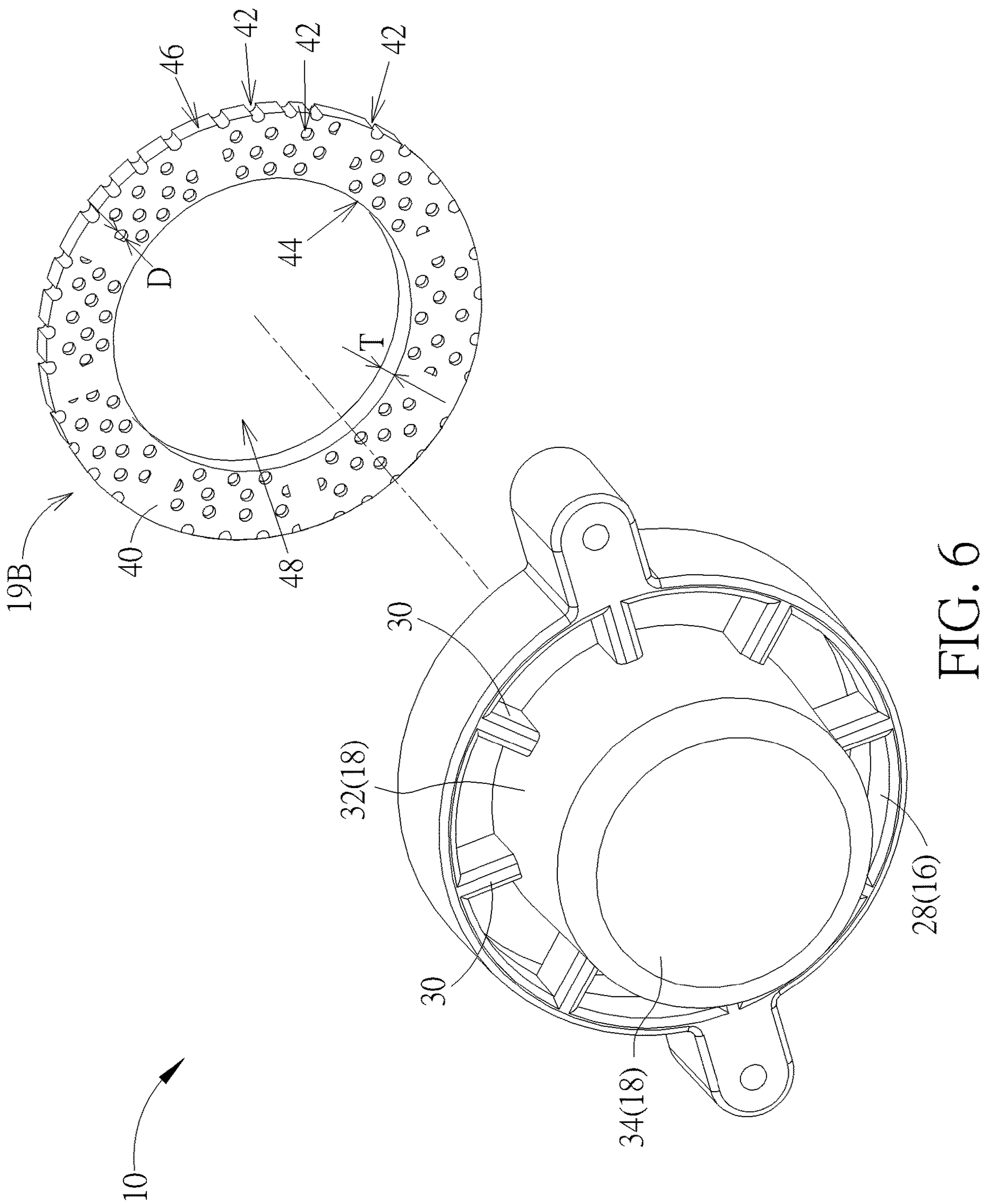
FIG. 6 is a diagram of the partial case of the smoke detector and the perforated plate according to a third embodiment of the present invention.

Please refer to FIG. 6. FIG. 6 is a diagram of the partial case of the smoke detector 10 and the perforated plate 19B according to a third embodiment of the present invention. In the third embodiment, elements having the same numerals as ones of the foresaid embodiments can have the same structures and functions, and a detailed description is omitted herein for simplicity. The perforated plate 19B can be the ring-typed structure, and have the plate body 40, the hole 42, the inner edge 44 and the outer edge 46. The holes 42 can be distributed on several sections of the plate body 40. The inner edge 44 and the outer edge 46 of the perforated plate 19B can be respectively attached to the lateral wall 32 and the second block structure 28, and a thickness T of the plate body 40 can be preferably greater than or equal to an aperture D of the hole 42; that is to say, the perforated plate 19B can have the deeper hole 42 that can prevent the insect from passing so as provide the enhanced anti-insect function.

Figure 7:
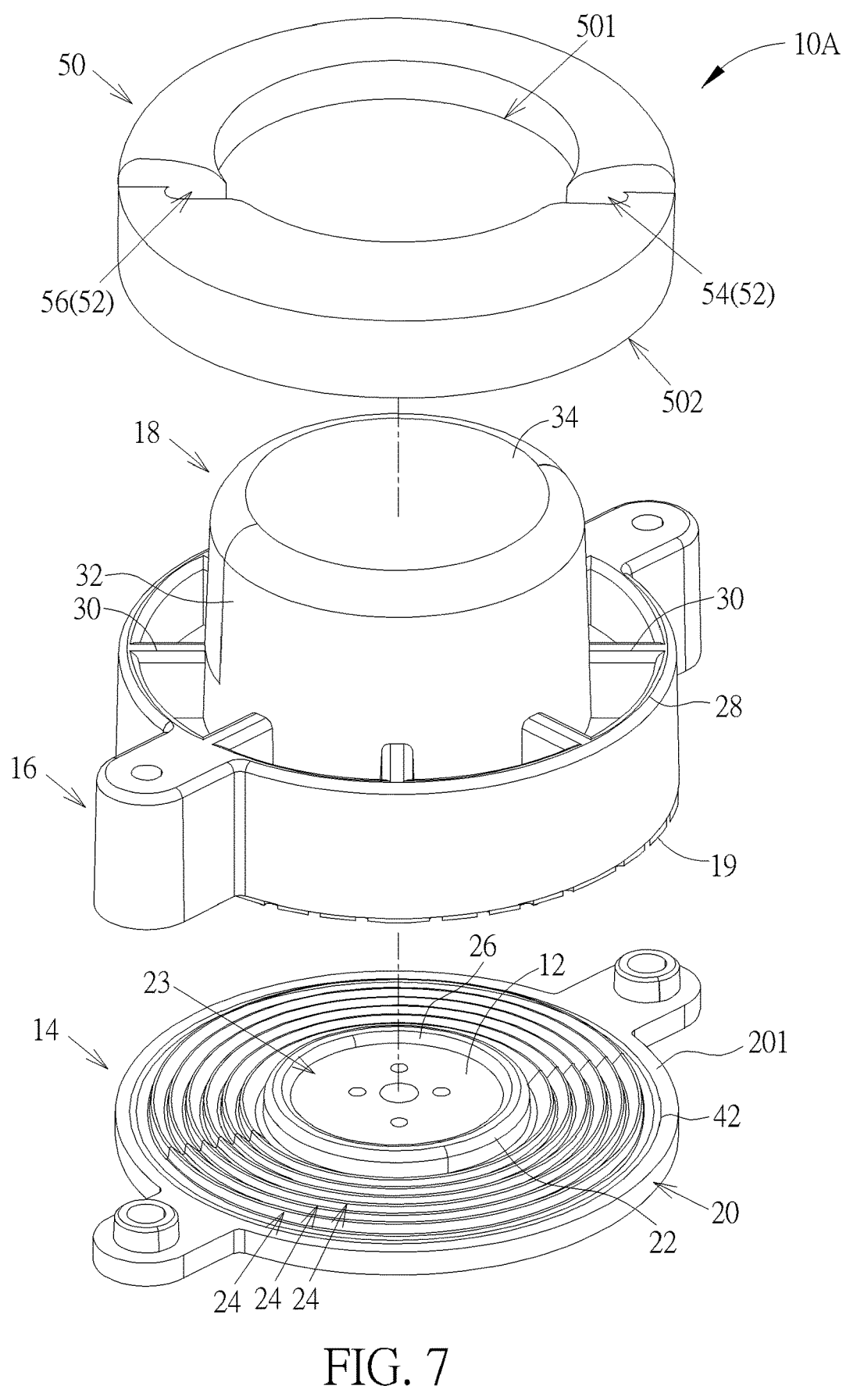

Please refer to FIG. 7. FIG. 7 is an exploded diagram of a smoke detector 10A according to another embodiment of the present invention. The smoke detector 10A can at least include the optical detection module 12, the substrate 14, the base 16, the top cover 18 and a spoiler element 50, and further optionally include the perforated plate 19. In the embodiment, elements having the same numeral as ones of the foresaid embodiment have the same structures and functions, and the detailed description is omitted herein for simplicity. The spoiler element 50 can be disposed on a side of the base 16 opposite to the substrate 14 to cover the guiding channel formed between the top cover 18 and the base 16 via the connection rib 30, or can be disposed on a side of the connection rib 30 opposite to the perforated plate 19.

The spoiler element 50 can have some guiding hole structures 52, and arrangement of the guiding hole structures 52 can conform to asymmetric design at 360 degrees. The guiding hole structure 52 can be disposed on the side of the spoiler element 50 opposite to the base 16 for connecting with the guiding channel. Moreover, an inlet 54 and an outlet 56 of the guiding hole structure 52 can be connected with inner space of the base 16, so as to be a spoiler mechanism for controlling, speeding and stabilizing smoke flow around the smoke detector 10A.

The spoiler element 50 can be a ring-shaped structure, and an inner side 501 and an outer side 502 of the spoiler element 50 can respectively abut against the lateral wall 32 of the top cover 18 and the second block structure 28 of the base 16 for covering the guiding channel. In any possible embodiments, the spoiler element 50 can be designed as a detachable form or a non-detachable form. The spoiler element 50 in the detachable form may directly press on the connection rib 30, and assembled with the top cover 18 and the base 16 in an engagement manner or other suitable manners. The spoiler element 50 in the non-detachable form can be monolithically integrated with the top cover 18.

Figure 8:
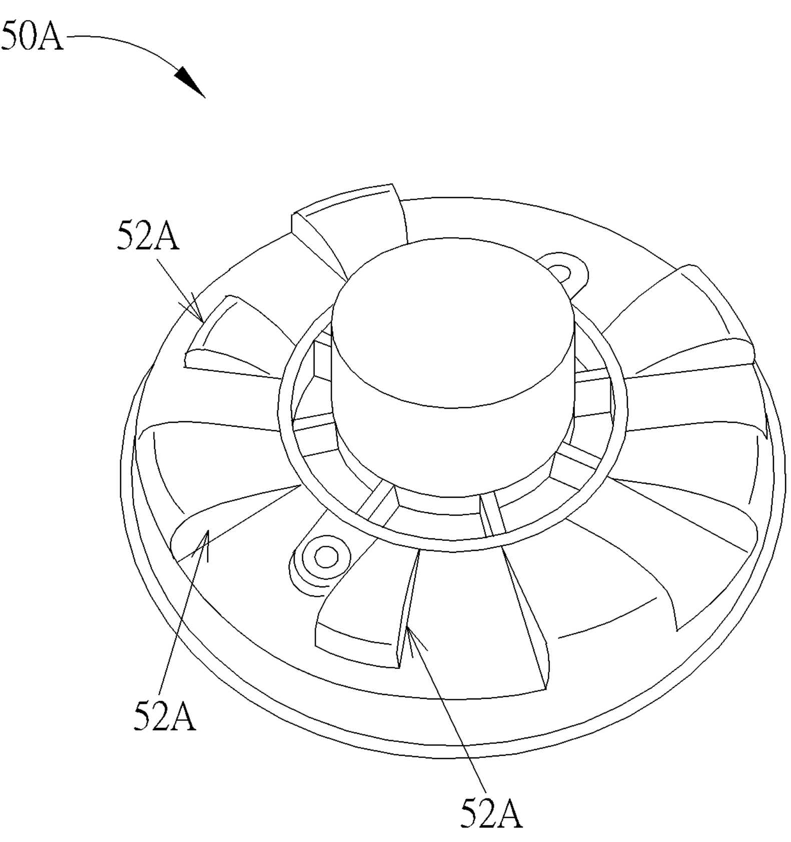
FIG. 8 and FIG. 9 are diagrams of the spoiler element according to other embodiments of the present invention.
Figure 9:
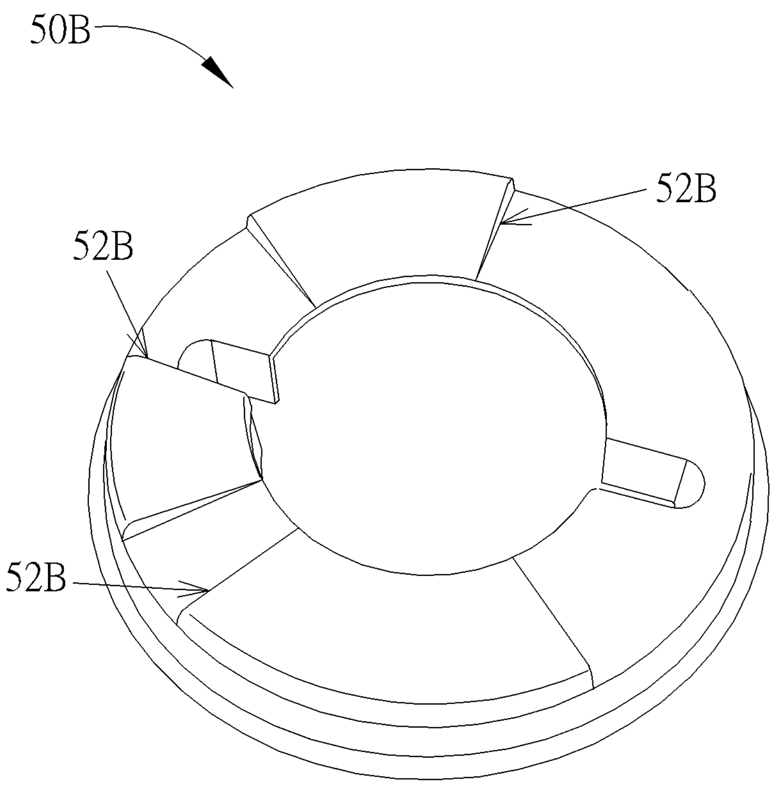

Please refer to FIG. 8 and FIG. 9. FIG. 8 and FIG. 9 are diagrams of the spoiler elements 50A and 50B according to other embodiments of the present invention. Functions and arrangement of the spoiler elements 50A and 50B can be similar to the functions and the arrangement of the spoiler element 50, and the detailed description is omitted herein for simplicity. A number and a shape of the guiding hole structures 52A and 52B respectively formed on the spoiler elements 50A and 50B may be different from the number and the shape of the guiding hole structure 52, and still can be used as the spoiler mechanism for controlling, speeding and stabilizing the smoke flow around the smoke detector 10A.

The asymmetric design of the guiding hole structures at 360 degrees can be interpreted as: numbers of the guiding hole structures 52, 52A and 52B can preferably be as odd number. At least two guiding hole structures 52, 52A and 52B can have different hole sizes, and an interval between two adjacent guiding hole structures 52, 52A and 52B can be different from an interval between other adjacent guiding hole structures 52, 52A and 52B. For example, the spoiler element 50A can have the large-size guiding hole structure 52A and the small-size guiding hole structure 52A, as shown in FIG. 8; the interval between two adjacent guiding hole structures 52B of the spoiler element 50B can be different from the interval between other adjacent guiding hole structures 52B, as shown in FIG. 9. The embodiment shown in FIG. 8 can be integrated with the embodiment shown in FIG. 9, which means a possible embodiment can have the guiding hole structures with the large-size and the small-size, and the interval between two adjacent guiding hole structures can be different from the interval between other adjacent guiding hole structures.

In conclusion, the present invention can utilize the substrate, the base and the top cover to form the case of the smoke detector. The optical detection module can be disposed on the central detection region of the substrate and surrounded by the first block structure. The second block structure of the base can be partly overlapped with the lateral wall of the top cover. The perforated plate can be disposed between the lateral wall and the second block structure, and used to shield the guiding channel formed between the base and the top cover. The aperture of the hole on the perforated plate can be smaller than the size of the common insects, and can avoid the insect from passing through the guiding channel to enter the top cover. The perforated plate can be detachable, or integrated with other structural components. Therefore, the present invention can replace the original perforated plate by another perforated plate having the holes with the suitable aperture and the suitable distribution density in accordance with the insect species lived in the place where on the smoke detector is installed, for preferred anti-insect function.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A smoke detector with an anti-insect function comprising:

a substrate, having a ring shape region surrounding a central detection region, and a first block structure of the central detection region being protruded from the substrate and higher than an upper surface of the ring shape region;

an optical detection module disposed inside the central detection region and surrounded by the first block structure;

a top cover having a lateral wall;

a base disposed on the substrate and connected with the top cover and adapted to cover the optical detection module, the base having a second block structure surrounding the top cover and partly overlapped with the lateral wall to form a guiding channel; and a perforated plate disposed between the lateral wall and the second block structure and adapted to prevent an insect from moving into the top cover through the guiding channel.

2. The smoke detector of claim 1, wherein the perforated plate is a ring-typed structure, an inner edge of the ring-typed structure corresponds to the lateral wall, an outer edge of the ring-typed structure corresponds to the second block structure, a plurality of holes is formed on a plate body of the ring-typed structure set between the inner edge and the outer edge.

3. The smoke detector of claim 2, wherein the central detection region comprises a sunken structure, the optical detection module is disposed inside the sunken structure, and a hollow area formed by the inner edge of the ring-typed structure corresponds to the optical detection module.

4. The smoke detector of claim 2, wherein the inner edge and the outer edge of the ring-typed structure respectively abuts against the lateral wall and the second block structure.

5. The smoke detector of claim 2, wherein a thickness of the plate body is greater than or equal to an aperture of each of the plurality of hole.

6. The smoke detector of claim 1, wherein the top cover further comprises a cover body connected to the lateral wall, the lateral wall and the cover body both have an airtight feature, and the perforated plate is attached to a side of the lateral wall opposite to the cover body.

7. The smoke detector of claim 1, wherein the smoke detector further comprises a plurality of connection ribs, two opposite ends of each of the plurality of connection ribs are connected to an inner surface of the base and an outer surface of the top cover respectively, and the perforated plate is attached to the plurality of connection ribs.

8. The smoke detector of claim 1, wherein the perforated plate is connected to the top cover and the base in a monolithically integrated manner.

9. The smoke detector of claim 1, wherein the perforated plate is disposed between the top cover and the base in a detachable manner.

* * * * *